United States Patent [19]
Bru-Magniez et al.

[11] Patent Number: 5,663,181
[45] Date of Patent: *Sep. 2, 1997

[54] NAPHTHYRIDINE DERIVATIVES, THEIR METHODS OF PREPARATION AND PHARMACEUTICAL COMPOSITIONS IN WHICH THEY ARE PRESENT, USEFUL ESPECIALLY AS ANTIPROLIFERATIVE DRUGS

[75] Inventors: Nicole Bru-Magniez, Paris; Michèle Launay, Rueil Malmaison; Jean-Marie Teulon, La Celle Saint Cloud, all of France

[73] Assignee: Laboratoires UPSA, Agen, France

[*] Notice: The term of this patent shall not extend beyond the expiration date of Pat. No. 5,364,860.

[21] Appl. No.: 549,665

[22] PCT Filed: Jun. 24, 1994

[86] PCT No.: PCT/FR94/00763

§ 371 Date: Nov. 29, 1995

§ 102(e) Date: Nov. 29, 1995

[87] PCT Pub. No.: WO95/00513

PCT Pub. Date: Jan. 5, 1995

Related U.S. Application Data

[63] Continuation-in-part of Ser. No. 97,239, Jul. 27, 1993, Pat. No. 5,364,860.

[30] Foreign Application Priority Data

Jun. 25, 1993 [FR] France .................. 93 07746

[51] Int. Cl.$^6$ .................. A61K 31/44; C07D 471/02
[52] U.S. Cl. .................. 514/300; 546/122
[58] Field of Search .................. 514/300; 546/122

[56] References Cited

U.S. PATENT DOCUMENTS 5,302,606  4/1994  Spada .................. 514/357

FOREIGN PATENT DOCUMENTS 0 267 691  5/1988  European Pat. Off. .

OTHER PUBLICATIONS

Bilder GE, Krawiec JA, McVety K, Gazit A, Gilon C, Lyall R, Zilbertstein A, Levitski A, Perrone MH, Schrieber AB. Am. J. Physiol. 260, pp. C721–C730 1991.

*Primary Examiner*—C. Warren Ivy
*Assistant Examiner*—Evelyn Huang
*Attorney, Agent, or Firm*—Armstrong, Westerman, Hattori, McLeland & Naughton

[57] ABSTRACT

The present invention relates to the derivatives of the formula

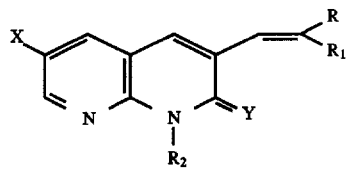

and their addition salts, and to their use in therapeutics, especially as drugs having antiproliferative properties and affording an effective treatment for diseases such as cancer, psoriasis, atherosclerosis, restenosis phenomena or any other pathological condition due to cell proliferation.

10 Claims, No Drawings

NAPHTHYRIDINE DERIVATIVES, THEIR METHODS OF PREPARATION AND PHARMACEUTICAL COMPOSITIONS IN WHICH THEY ARE PRESENT, USEFUL ESPECIALLY AS ANTIPROLIFERATIVE DRUGS

This application is a national stage application under 35 USC 371 of International Application Number PCT/FR94/00763 filed Jun. 24, 1994, and is also a continuation-in-part of application Ser. No. 08/097,239 filed Jul. 27, 1993, now U.S. Pat. No. 5,364,860.

The present invention relates, by way of novel products, to the naphthyridine derivatives of general formula (I) below and their addition salts, in particular the pharmaceutically acceptable addition salts.

The compounds of the invention, which possess antiproliferative properties, can be used in the treatment of cancer, psoriasis, atherosclerosis, restenosis phenomena or any other pathological condition due to cell proliferation in mammals and especially in man.

The present invention further relates to the method of preparing said products and to their applications in therapeutics.

These naphthyridine derivatives have general formula (I):

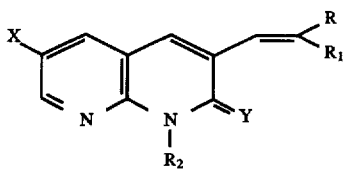

Formula (I)

in which:
X is:
  the hydrogen atom or
  a halogen atom;
Y is:
  the oxygen atom,
  the sulfur atom or
  an NH group;
R and $R_1$ are non-simultaneously:
  a hydrogen atom,
  a CN radical,
  a group COOR', R' being a hydrogen atom or a lower alkyl radical having 1 to 6 carbon atoms,
  a $CONH_2$ group,
  a group

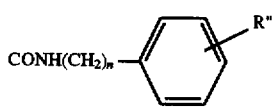

in which n is an integer from 0 to 5 and R" is the hydrogen atom, a halogen atom or a lower alkyl radical having 1 to 6 carbon atoms,
  an $NO_2$ radical,
  a pyridine ring which is unsubstituted or substituted by a halogen atom, or
  a thiazole ring which is unsubstituted or substituted by a lower alkyl radical having 1 to 6 carbon atoms,
or R and $R_1$ together form indolin-2-one; and $R_2$ is:
  a lower alkyl radical having 1 to 6 carbon atoms, a lower cycloalkyl radical having 3 to 7 carbon atoms, or
a group

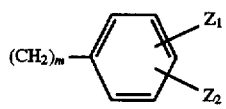

in which m is an integer from 0 to 5 and $Z_1$ and $Z_2$ are independently:

the hydrogen atom,
  a lower alkyl radical having 1 to 6 carbon atoms,
  a halogen atom,
  a trifluoromethyl radical,
  an OH radical,
  a lower O-alkyl radical having 1 to 6 carbon atoms,
  a lower S-alkyl radical having 1 to 6 carbon atoms,
  an $NO_2$ radical,
  an $NH_2$ radical or
  a CN radical.

In the description and the claims, lower alkyl is understood as meaning a linear or branched hydro-carbon chain having from 1 to 6 carbon atoms. A lower alkyl radical is for example a methyl, ethyl, propyl, isopropyl, butyl, isobutyl, tert-butyl, pentyl, isopentyl, hexyl or isohexyl radical.

$C_3$—$C_7$—Cycloalkyl radical is understood as meaning a saturated cyclic hydrocarbon radical, preferably a cyclopropyl, cyclobutyl, cyclopentyl, cyclohexyl or cycloheptyl radical.

Halogen is understood as meaning a chlorine, bromine, iodine or fluorine atom.

The following abbreviations have been used in the description:

Phe: phenyl
i-Pr: isopropyl (1-methylethyl)
Bn: benzyl
Py: pyridyl
Thz: thiazole Advantageously, within the framework of the present invention, a compound of formula (I) will be used in which at least one of the following conditions is satisfied:

X is the hydrogen atom
  X is the chlorine atom
  Y is the oxygen atom
  R is a pyridine
  R is a chloropyridine
  $R_1$ is the CN radical
  $R_2$ is the 3,5-dichlorophenyl group
  $R_2$ is the 4-methoxyphenyl group
  $R_2$ is the 3-chlorophenyl group The particularly preferred compounds of the invention are selected from the products of the formulae:

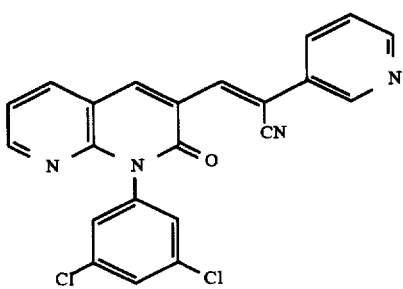

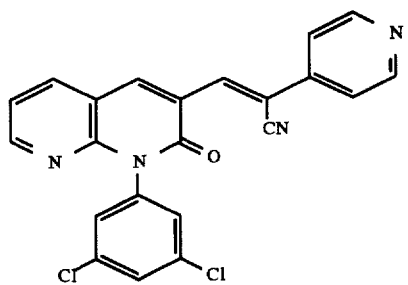

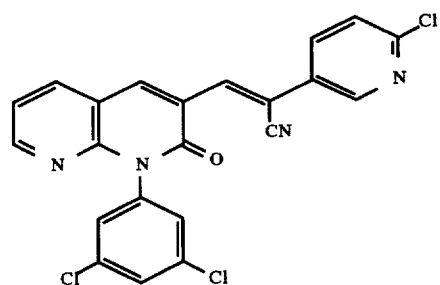

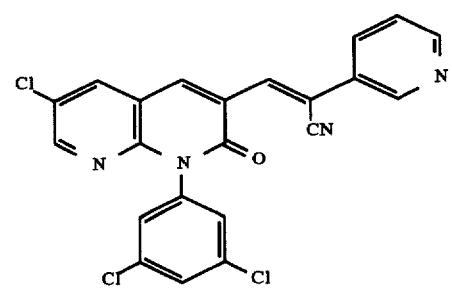

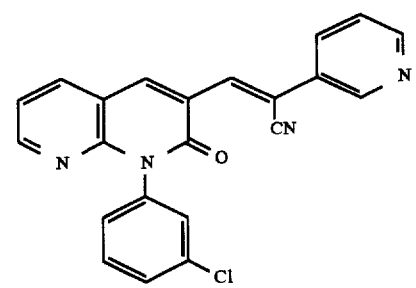

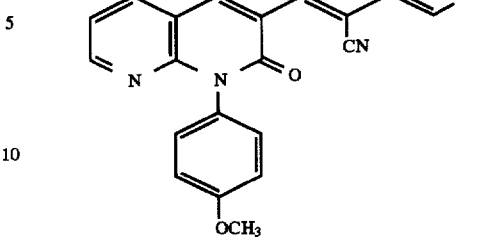

According to the invention, the compounds of formula (I) may be synthesized in the following manner:

The reaction of a 2-chloronicotinic acid of formula (II):

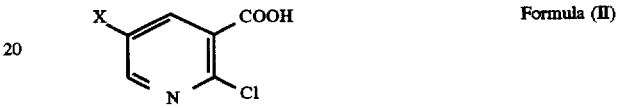

Formula (II)

or one of its esters, in which X is as defined above, with an amine of formula (III):

$NH_2—R_2$

Formula (III)

in which $R_2$ is as defined above, by heating without a solvent or in a solvent such as, for example, toluene or xylene or an alcohol, will give the 2-aminonicotinic acids of formula (IV):

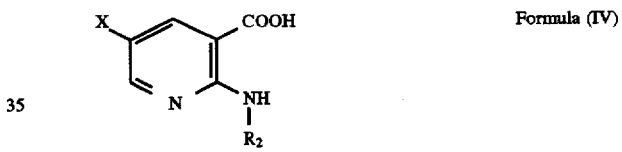

Formula (IV)

or one of their esters, in which X and $R_2$ are as defined above, according to a method known in the literature: U.S. Pat. No. 3,415,834; C. Hoffmann, A. Faure, Bull. Soc. Chim. France 1966, 2316.

The reduction of an acid of formula (IV) or one of its esters, for example the methyl or ethyl ester, with a conventional reducing agent such as, for example, lithium aluminum hydride, in an organic solvent such as, for example, tetrahydrofuran or ethyl ether, will give the alcohols of formula (V):

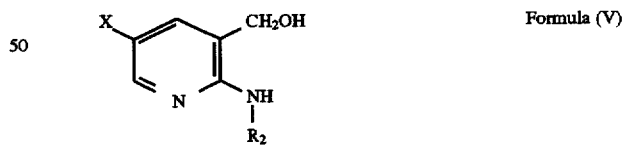

Formula (V)

in which X and $R_2$ are as defined above.

In the case where $R_2$ carries a substituent sensitive to certain reducing agents, such as nitro or cyano, for example, the reducing agent chosen for reducing the ester will be one which does not affect this substituent, for example lithium borohydride prepared in situ from potassium borohydride and lithium chloride in tetrahydrofuran, or else sodium borohydride in dioxane.

The oxidation of an alcohol of formula (V) with a mild oxidizing agent such as, for example, $MnO_2$, in an organic solvent such as dichloromethane, chloroform, toluene or xylene, at a temperature between 20 and 80° C., will give the nicotinaldehydes of formula (VI):

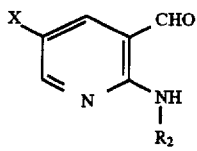

Formula (VI)

in which X and $R_2$ are as defined above.

The reaction of the aldehydes of formula (VI) with an alkyl dialkoxypropionate of formula (VII):

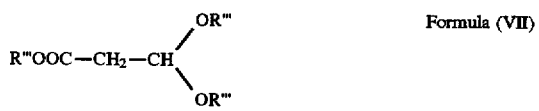

Formula (VII)

in which R''' is a lower alkyl radical having 1 to 6 carbon atoms, optimally the methyl radical, or else with a dialkoxypropionitrile of formula (VII'):

Formula (VII')

in which R''' is as defined in formula (VII), in tetrahydrofuran, in the presence of a sodium or potassium alcoholate, will give the derivatives of formula (VIII):

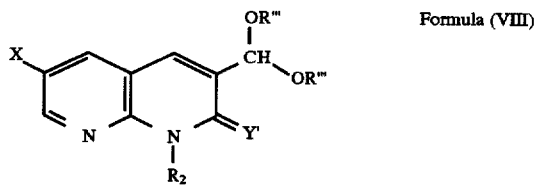

Formula (VIII)

in which X, $R_2$ and R''' are as defined above and Y' is an oxygen atom in the case where the reaction has been carried out with the compound of formula (VII), or an NH group in the case where the reaction has been carried out with the compound of formula (VII').

The dialkylacetal derivatives of formula (VIII) will be hydrolyzed, for example by reaction with hydrochloric acid in a solvent such as tetrahydrofuran, to give the aldehydes of formula (IX):

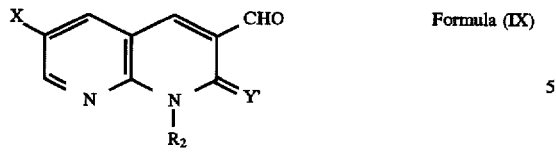

Formula (IX)

in which X, $R_2$ and Y' are as defined above.

The reaction of the aldehydes of formula (IX) with an activated methylene of formula (X): in which R and $R_1$ are as defined in formula (I), according to the conventional methods of the Knoevenagel reaction, for example by heating in an alcohol such as methanol or ethanol, in the presence of piperidine, a sodium or potassium alcoholate or sodium or potassium carbonate, will give the compounds of formula (XI):

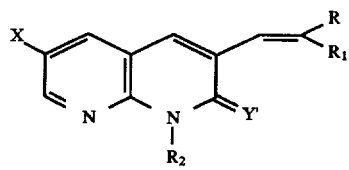

Formula (XI)

in which X, R, $R_1$, Y' and $R_2$ are as defined above.

These derivatives of formula (XI) are derivatives of formula (I) and, by treatment with $P_4S_{10}$ in xylene under reflux, the derivatives of formula (XI) in which Y' is the oxygen atom may give the derivatives of formula (I) in which Y is the sulfur atom. The derivatives of formula (I) in which $R_2$ possesses a nitro group may be reduced to derivatives in which $R_2$ possesses an amino group.

In certain cases, the reaction of the aldehyde of formula (IX) with the nitrile of formula (X) will give the hydroxylated compounds of formula (XII):

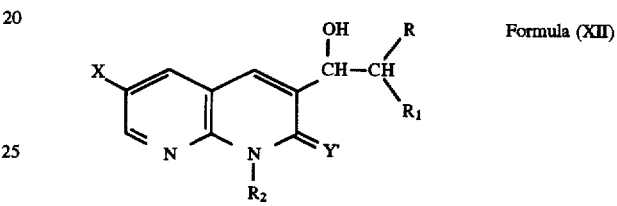

Formula (XII)

in which X, R, $R_1$, Y' and $R_2$ are as defined above, instead of giving the ethylenic compounds of formula (XI) directly.

In this case, the derivatives of formula (XII) will be dehydrated to compounds of formula (XI) by methods known to those skilled in the art, for example by reaction with trifluoroacetic anhydride and trifluoroacetic acid or else with paratoluenesulfonic acid in a solvent such as dichloromethane or chloroform, or else toluene or xylene, at a temperature between 20 and 130° C.

The compounds of formula (I) as defined above, and their addition salts, in particular the pharmaceutically acceptable addition salts, possess a very good antiproliferative activity.

These properties justify their application in therapeutics and the invention further relates, by way of drugs, to the products as defined by formula (I) above, and their addition salts, in particular the pharmaceutically acceptable addition salts.

Addition salts of some of the compounds of formula (I) can be obtained by reacting these compounds with a mineral or organic acid by a method known per se. Among the acids which can be used for this purpose, there may be mentioned hydrochloric, hydrobromic, sulfuric, phosphoric, toluene-4-sulfonic, methane-sulfonic, cyclohexylsulfamic, oxalic, succinic, formic, fumaric, maleic, citric, aspartic, cinnamic, lactic, glutamic, N-acetylaspartic, N-acetylglutamic, ascorbic, malic, benzoic, nicotinic and acetic acids.

Thus the invention also covers a pharmaceutical composition which comprises a pharmaceutically effective amount of at least one compound of formula (I) as defined above, or one of its pharmaceutically acceptable addition salts, which may or may not be incorporated in a pharmaceutically acceptable excipient, vehicle or carrier.

These compositions can be administered by the buccal, rectal, parenteral, transdermal or ocular route.

These compositions can be solid or liquid and can be presented in the pharmaceutical forms commonly used in human medicine, such as, for example, simple or coated tablets, gelatin capsules, granules, suppositories, injectable preparations, transdermal systems and eye lotions. They are prepared by the customary methods. The active principle, which consists of a pharmaceutically effective amount of at least one compound of formula (I) as defined above, or one of its pharmaceutically acceptable addition salts, can be incorporated therein with excipients normally employed in these pharmaceutical compositions, such as talc, gum arabic, lactose, starch, magnesium stearate, polyvidone, cellulose derivatives, cacao butter, semisynthetic glycerides, aqueous or non-aqueous vehicles, fatty substances of animal or vegetable origin, glycols, various wetting agents, dispersants or emulsifiers, silicone gels, certain polymers or copolymers, preservatives, flavorings and colors.

The invention also covers an antiproliferative pharmaceutical composition affording especially a favorable treatment for any pathological condition due to cell proliferation, which comprises a pharmaceutically effective amount of at least one compound of formula (I) given above, or one of its pharmaceutically acceptable addition salts, which may or may not be incorporated in a pharmaceutically acceptable excipient, vehicle or carrier.

The invention also covers a method of preparing a pharmaceutical composition, which comprises incorporating a pharmaceutically effective amount of at least one compound of formula (I) as defined above, or one of its pharmaceutically acceptable addition salts, into a pharmaceutically acceptable excipient, vehicle or carrier. In one embodiment, a pharmaceutical composition with antiproliferative activity is prepared which affords especially a favorable treatment for cancer, psoriasis, atherosclerosis, restenosis phenomena or any other pathological condition due to cell proliferation.

In one variant, a composition is formulated as gelatin capsules or tablets containing from 1 mg to 1000 mg of active ingredient, or as injectable preparations containing from 0.1 mg to 500 mg of active ingredient. Formulations as suppositories, ointments, creams, gels, aerosol preparations or eye lotions may also be used.

The invention also covers a method of therapeutic treatment for mammals, which comprises administering to this mammal a therapeutically effective amount of at least one compound of formula (I) as defined above, or one of its pharmaceutically acceptable addition salts. In one variant of this method of treatment, the compound of formula (I), either by itself or in association with a pharmaceutically acceptable excipient, is formulated as gelatin capsules or tablets containing from 1 mg to 1000 mg of active ingredient for oral administration, or as injectable preparations containing from 0.1 to 500 mg of active ingredient, or else as suppositories, ointments, creams, gels, aerosol preparations or eye lotions.

In human and animal therapeutics, the compounds of formula (I) and their salts can be administered by themselves or in association with a physiologically acceptable excipient, in any form, in particular in the form of gelatin capsules or tablets for oral administration or in the form of an injectable solution for parenteral administration. Other forms of administration, such as suppositories, ointments, creams, gels, aerosol preparations or eye lotions, can be envisaged.

As will be clearly apparent from the pharmacological tests given at the end of the description, the compounds according to the invention can be administered in human therapeutics for the abovementioned indications, orally in the form of tablets or gelatin capsules containing from 1 mg to 1000 mg of active ingredient, or parenterally in the form of injectable preparations containing from 0.1 mg to 500 mg of active ingredient, in one or more daily dosage units for an adult with an average weight of 60 to 70 kg.

In animal therapeutics, the daily dose which can be used is between 0.1 and 100 mg per kg.

Further characteristics and advantages of the invention will be understood more clearly from the following description of some Examples, which in no way imply a limitation but are given by way of illustration.

EXAMPLE 1

2-(3-Trifluoromethylphenyl)amino-3-hydroxymethylpyridine

Formula (V): X=H; $R_2$=3—$CF_3$-phenyl

A solution of 200 g of 2-(3-trifluoromethyl-phenyl) aminonicotinic acid in 500 ml of anhydrous tetrahydrofuran is added dropwise to a suspension of 52 g of lithium aluminum hydride in 1000 ml of anhydrous ethyl ether. When the addition is complete, the reaction mixture is refluxed for 3 h. After cooling, the excess hydride is destroyed by the addition of ethyl acetate followed by a saturated aqueous solution of sodium sulfate. The precipitate formed is filtered off and washed with ether. The combined filtrates are evaporated under vacuum and 185.2 g of 2-(3-trifluoromethylphenyl)amino-3-hydroxymethylpyridine are recovered in the form of crystals melting at 103–105° C.

The following derivatives of formula (V) are prepared by this method:

| Example | X | $R_2$ | M.p. (°C.) | Yield (%) |
|---|---|---|---|---|
| 2 | H | Phenyl | Oil | 95 |
| 3 | H | 4-F-Phe | 89–90 | 88 |
| 4 | H | 3-$SCH_3$-Phe | Oil | 95 |
| 5 | H | 2,5-F-Phe | 71–74 | 98 |
| 6 | H | 3-$OCH_3$-Phe | 94–95 | 98 |
| 7 | H | 3-Cl-Phe | 114–115 | 94 |
| 8 | H | 4-Cl-Phe | 124–126 | 95 |
| 9 | H | 3,5-Cl-Phe | 149 | 90 |
| 10 | H | 4-$OCH_3$-Phe | 93 | 86.5 |
| 11 | H | 3-$CH_3$-Phe | Oil | 92 |
| 12 | H | 4-$CH_3$-Phe | Oil | 98 |

EXAMPLE 13

2-(3-Cyanophenyl)amino-3-hydroxymethylpyridine

Formula (V): X=H; $R_2$=3-CN-phenyl 8 g of lithium chloride are added in small portions, with stirring, to a solution of 39.3 g of methyl 2-(3-cyanophenyl) aminonicotinate in 600 ml of tetrahydrofuran containing 10 g of potassium borohydride. When the addition is complete, the mixture is refluxed for 4 h and then concentrated under vacuum. After the addition of water and ice to the residue obtained, extraction is carried out with ether and the ether phase is washed with water and then dried over sodium sulfate.

After evaporation of the ether, 31.6 g of 2-(3-cyanophenyl)amino-3-hydroxymethylpyridine are obtained in the form of crystals melting at 126° C.

The following derivatives of formula (V) are prepared by this method:

| Example | X | $R_2$ | M.p. (°C.) | Yield (%) |
|---|---|---|---|---|
| 14 | H | 3-$No_2$-Phe | 162 | 84 |
| 15 | H | 3-CN-4-Cl-Phe | 147 | 90 |
| 16 | H | 3-CN-4-F-Phe | 126 | 90 |
| 17 | H | 4-CN-Phe | 142 | 94 |
| 18 | H | i-Pr | 91 | 47 |
| 19 | Cl | 3,4-$OCH_3$-Bn | 127 | 78 |
| 20 | Cl | 3,4-Cl-Phe | 166 | 48 |
| 21 | H | Cyclohexyl | Oil | 94 |

EXAMPLE 22

2-(3-Trifluoromethylphenyl)aminonicotinaldehyde

Formula (VI): X=H; $R_2$=3—$CF_3$-phenyl 690 g of $MnO_2$ are added in small portions to a solution of 185 g of 2-(3-trifluoromethylphenyl)amino-3-hydroxymethylpyridine, prepared in Example 1, in 2300 ml of chloroform. When the addition is complete, the mixture is stirred at room temperature for 6 h. The reaction medium is then filtered on Celite and the filtrate is evaporated to dryness. The resulting crystals, weighing 175 g, are recrystallized from heptane. 160 g of 2-(3-trifluoromethylphenyl)aminonicotinaldehyde are thus recovered in the form of crystals melting at 80–81° C.

The following derivatives of formula (VI) are prepared by this method:

| Example | X | $R_2$ | M.p. (°C.) | Yield (%) |
|---|---|---|---|---|
| 23 | H | Phenyl | 77–78 | 80 |
| 24 | H | 3-CN-Phe | 153–154 | 60 |
| 25 | H | 4-F-Phe | 67–68 | 71 |
| 26 | H | 3-SCH$_3$-Phe | 63–64 | 70 |
| 27 | H | 2,5-F-Phe | 129–130 | 76 |
| 28 | H | 3-OCH$_3$-Phe | 65–66 | 75 |
| 29 | H | 3-Cl-Phe | 99–100 | 78 |
| 30 | H | 3-NO$_2$-Phe | 166 | 76 |
| 31 | H | 3-CH$_3$-Phe | 95–97 | 79 |
| 32 | H | 3-CN-4-Cl-Phe | 203 | 60 |
| 33 | H | 3-CN-4-F-Phe | 193 | 80 |
| 34 | H | 4-Cl-Phe | 101–102 | 60 |
| 35 | H | 3,5-Cl-Phe | 159 | 92 |
| 36 | H | 4-OCH$_3$-Phe | 84 | 54 |
| 37 | H | 2-Cl-Phe | 101 | 70 |
| 38 | H | 4-CH$_3$-Phe | 55–58 | 72 |
| 39 | 5-Cl | 3,5-Cl-Phe | 183 | 81 |
| 40 | H | 4-CN-Phe | 166 | 93 |
| 41 | H | i-Pr | Oil | 84 |
| 42 | 5-Cl | 3,4-OCH$_3$-Bn | 114 | 42 |
| 43 | H | Cyclohexyl | Oil | 73 |

EXAMPLE 44

1-(3,5-Dichlorophenyl)-1,2-dihydro-3-dimethoxymethyl-2-oxo-1,8-naphthyridine

Formula (VIII): X=H; R'''=$CH_3$; Y'=O; $R_2$=3,5-Cl-phenyl

A solution of 42.7 g of 2-(3,5-dichlorophenyl)-aminonicotinaldehyde, prepared in Example 35, in 500 ml of tetrahydrofuran containing 35.6 g of methyl 3,3-dimethoxypropionate, and a solution of sodium methylate prepared from 5.5 g of sodium in 100 ml of methanol, are stirred for 24 h at room temperature. The reaction mixture is subsequently concentrated under vacuum, water is then added and the crystals formed are filtered off, washed carefully with water and dried to give 44.25 g of 1-(3,5-dichlorophenyl)-1,2-dihydro-3-dimethoxymethyl-2-oxo-1,8-naphthyridine in the form of white crystals melting at 190° C. Yield 75.7%.

The following derivatives of formula (VIII) are prepared by this method:

| Example | X | $R_2$ | R''' | Y' | M.p. (°C.) | Yield (%) |
|---|---|---|---|---|---|---|
| 45 | H | 4-OCH$_3$-Phe | CH$_3$ | O | 210 | 58 |
| 46 | H | 3-Cl-Phe | CH$_3$ | O | 112–118 | 70 |
| 47 | H | 2-Cl-Phe | CH$_3$ | O | 125 | 51 |
| 48 | H | 3-CH$_3$-Phe | CH$_3$ | O | 398 | 57 |
| 49 | H | 4-CH$_3$-Phe | CH$_3$ | O | 108 | 17 |
| 50 | H | 3-SCH$_3$-Phe | CH$_3$ | O | 155 | 78 |
| 51 | H | 4-CN-Phe | CH$_3$ | O | 152–153 | 64 |
| 52 | H | Phenyl | CH$_3$ | O | 146 | 58 |
| 53 | H | 3-CF$_3$-Phe | CH$_3$ | O | 143 | 67 |
| 54 | H | 3-NO$_2$-Phe | CH$_3$ | O | 198 | 55 |
| 55 | H | 3,5-Cl-Phe | CH$_3$ | O | 194 | 67 |
| 56 | H | i-Pr | CH$_3$ | O | Oil | — |
| 57 | H | 3,4-OCH$_3$-Bn | CH$_3$ | O | 123 | 49 |
| 58 | H | Cyclohexyl | CH$_3$ | O | Oil | — |

EXAMPLE 59

1,2-Dihydro-3-dimethoxymethyl-2-imino-1-(4-methoxyphenyl)-1,8-naphthyridine

Formula (VIII): X=H; R'''=$CH_3$; Y'=NH; $R_2$=4-OCH$_3$-phenyl

The procedure of Example 44 using 14.6 g of 2-(4-methoxyphenylamino)nicotinaldehyde and 11.15 g of 3,3-dimethoxypropionitrile (1.5 eq) gives, after washing of the resulting solid with ether, 10.5 g of 1,2-dihydro-3-dimethoxymethyl-2-imino-1-(4-methoxyphenyl)-1,8-naphthyridine in the form of an off-white solid melting at 167° C. Yield 50.6%.

EXAMPLE 60

[1-(3,5-Dichlorophenyl)-1,2-dihydro-2-oxo-1,8-naphthyridin-3-yl]carboxaldehyde

Formula (IX): X=H; Y'=O; $R_2$=3,5—Cl—phenyl

A suspension of 44.25 g of 1-(3,5-dichlorophenyl)-1,2-dihydro-3-dimethoxymethyl-1,8-naphthyridine, prepared in Example 44, in 450 ml of tetrahydrofuran and 66 ml of 10% aqueous hydrochloric acid (1.5 eq) is stirred at room temperature. The solid passes into solution and then a precipitate forms. After 24 h, the reaction mixture is concentrated under vacuum and the residue obtained is taken up with dichloromethane; the organic phase is washed with 10% sodium bicarbonate and then water and dried over magnesium sulfate. After concentration under vacuum, the solid obtained is taken up with ether and filtered off to give 35.3 g of [1-(3,5-dichlorophenyl)-1,2-dihydro-2-oxo-1,8-naphthyridin-3-yl]carboxaldehyde melting at 250° C. Yield 91%.

The following derivatives of formula (IX) are prepared by this method:

| Example | X | $R_2$ | Y' | M.p. (°C.) | Yield (%) |
|---|---|---|---|---|---|
| 61 | H | 4-OCH$_3$-Phe | O | 245 | 95 |
| 62 | H | 3-Cl-Phe | O | 223 | 94 |
| 63 | H | 2-Cl-Phe | O | 238 | 90 |
| 64 | H | 3-CH$_3$-Phe | O | 244 | 86 |
| 65 | H | 4-CH$_3$-Phe | O | 234 | 60 |
| 66 | H | 3-SCH$_3$-Phe | O | 204 | 74 |
| 67 | H | 4-CN-Phe | O | >250 | 83 |
| 68 | H | Phe | O | >250 | 90 |
| 69 | H | 3-CF$_3$-Phe | O | 220 | 90 |
| 70 | H | 3-NO$_2$-Phe | O | 263 | 90 |
| 71 | Cl | 3,5-Cl-Phe | O | 240 | 83 |
| 72 | H | i-Pr | O | 88 | 33 |
| 73 | Cl | 3,4-OCH$_3$-Bn | O | 191 | 89 |
| 74 | H | Cyclohexyl | O | 192–194 | 26 |

EXAMPLE 75

[1,2-Dihydro-1-(4-hydroxyphenyl)-2-oxo-1,8-naphthyridin-3-yl]carboxaldehyde

Formula (IX): X=H; Y'=O; $R_2$=4-OH-phenyl 10 g of [1-(4-methoxyphenyl)-1,2-dihydro-2-oxo-1,8-naphthyridin-3-yl]carboxaldehyde, prepared in Example 61, are dissolved in 300 ml of chloroform stabilized with amylene. The yellow solution is cooled to −30° C. and 71 ml of a 1 M solution of $BBr_3$ in dichloromethane are then added dropwise at this temperature, with stirring. The mixture is then left to warm up to room temperature and stirring is continued for 15 h. The reaction medium is hydrolyzed by the addition of 100 ml of water, after which the precipitate is filtered off, washed with water and then isopropanol and dried to give 8.6 g of [1-(4-hydroxyphenyl)-1,2-dihydro-2-oxo-1,8-naphthyridin-3-yl]carboxaldehyde in the form of a yellow solid melting at >250° C. Yield 90%.

EXAMPLE 76

[1,2-Dihydro-2-imino-1-(4-methoxyphenyl)-1,8-naphthyridin-3-yl]carboxaldehyde hydro-chloride Formula (IX): X=H; Y'=NH; $R_2$=4-$OCH_3$-phenyl 10.9 g of 1,2-dihydro-3-dimethoxymethyl-2-imino-1-(4-methoxyphenyl)-1,8-naphthyridine, prepared in Example 59, are suspended in 110 ml of tetrahydrofuran and the suspension is stirred. After the addition of 18.5 ml of 10% aqueous hydrochloric acid (1.5 eq), the solid passes into solution and then a precipitate is gradually observed. After 8 h, the solid is filtered off and washed with a small amount of tetrahydrofuran.

This gives 7.6 g of [1,2-dihydro-2-imino-1-(4-methoxyphenyl)-1,8-naphthyridin-3-yl]carboxaldehyde hydrochloride in the form of a pale yellow solid melting at 170° C. Yield 72%.

EXAMPLE 77

3-[1-(3,5-Dichlorophenyl)-1,2-dihydro-2-oxo-1,8-naphthyridin-3-yl]-3-hydroxy-2-(3-pyridyl)propionitrile Formula (XII): X=H; Y'=O; $R_2$=3,5-Cl-phenyl; R=3-pyridyl; $R_1$=CN 5.7 g of [1-(3,5-dichlorophenyl)-1,2-dihydro-2-oxo-1,8-naphthyridin-3-yl]carboxaldehyde, prepared in Example 60, are suspended in 60 ml of ethanol with 2.33 ml of 3-pyridylacetonitrile (1.2 eq) and a few drops of piperidine. The medium is refluxed for 4 h and then cooled. The solid formed is filtered off and washed with ethanol to give 7.2 g of 3-[1-(3,5-dichlorophenyl)-1,2-dihydro-2-oxo-1,8-naphthyridin-3-yl]-3-hydroxy-2-(3-pyridyl)propionitrile in the form of a white solid melting at 260° C. Yield 91%.

EXAMPLE 78

3-[1-(3,5-Dichlorophenyl)-1,2-dihydro-2-oxo-1,8-naphthyridin-3-yl]-2-(3-pyridyl)-prop-2-enenitrile Formula (I): X=H; Y=O; $R_2$=3,5-Cl-phenyl; R=3-pyridyl; $R_1$=CN 3 g of 3-[1-(3,5-dichlorophenyl)-1,2-dihydro-2-oxo-1,8-naphthyridin-3-yl]-3-hydroxy-2-(3-pyridyl)propionitrile, prepared in Example 77, are suspended in 20 ml of dichloromethane. After the addition of 1.05 ml of trifluoroacetic acid (2 eq), a yellow solution is obtained which becomes bright yellow with a rise in temperature after the addition of 1.44 ml of trifluoroacetic anhydride (1.5 eq). This solution is stirred for one hour and water is then added; the organic phase is decanted, washed with a 10% solution of sodium bicarbonate and then water and dried over magnesium sulfate. After concentration under vacuum, the solid obtained is washed with ether and dried to give 2.6 g of 3-[1-(3,5-dichlorophenyl)-1,2-dihydro-2-oxo-1,8-naphthyridin-3-yl]-2-(3-pyridyl)prop-2-enenitrile in the form of a bright yellow solid melting at 261° C. Yield 91%.

EXAMPLE 79

3-[1-(3,5-Dichlorophenyl)-1,2-dihydro-2-oxo-1,8-naphthyridin-3-yl]-2-(2-pyridyl)-prop-2-enenitrile Formula (I): X=H; Y=O; $R_2$=3,5-Cl-phenyl; R=2-pyridyl; $R_1$=CN 3.2 g of [1-(3,5-dichlorophenyl)-1,2-dihydro-2-oxo-1,8-naphthyridin-3-yl]carboxaldehyde, prepared in Example 60, are refluxed in 30 ml of ethanol with 1.4 ml of 2-pyridylacetonitrile (1.2 eq) and a few drops of piperidine.

After refluxing for 3 h, the reaction mixture is cooled and the bright yellow precipitate formed is filtered off and washed with ethanol to give 3.77 g of 3-[1-(3,5-dichlorophenyl)-1,2-dihydro-2-oxo-1,8-naphthyridin-3-yl]-2-(2-pyridyl)prop-2-enenitrile in the form of bright yellow crystals after purification by chromatography on a silica column (eluent: dichloromethane). Melting point 319° C. Yield 70%.

EXAMPLE 80

3-[1,2-Dihydro-1-(4-methoxyphenyl)-2-oxo-1,8-naphthyridin-3-yl]-2-(4-pyridyl)prop-2-enenitrile Formula (I): X=H; Y=O; $R_2$=4-$OCH_3$-phenyl; R=4-pyridyl; $R_1$=CN 2.8 g of [1,2-dihydro-1-(4-methoxyphenyl)-2-oxo-1,8-naphthyridin-3-yl]carboxaldehyde, prepared in Example 61, are added to a suspension of 1.6 g of 4-pyridylacetonitrile hydrochloride (1 eq) in 80 ml of ethanol containing 0.253 g of sodium (1.1 eq). The reaction mixture is refluxed for 3 h and then cooled to room temperature. The solid formed is filtered off, washed with ethanol and water and then recrystallized from methoxyethanol to give 1.3 g of 3-[1,2-dihydro-1-(4-methoxyphenyl)-2-oxo-1,8-naphthyridin-3-yl]-2-(4-pyridyl)prop-2-enenitrile in the form of bright yellow crystals melting at 283° C. Yield 34.5%.

EXAMPLE 81

3-[1-(3,5-Dichlorophenyl)-1,2-dihydro-2-oxo-1,8-naphthyridin-3-yl]-2-(4-pyridyl)-prop-2-enenitrile Formula (I): X=H; Y=O; $R_2$=3,5-Cl-phenyl; R=4-pyridyl; $R_1$=CN The procedure of Example 80 using 3.2 g of [1-(3,5-dichlorophenyl)-1,2-dihydro-2-oxo-1,8-naphthyridin-3-yl]carboxaldehyde gives, after recrystallization from methoxyethanol, 1.68 g of 3-[1-(3,5-dichlorophenyl)-1,2-dihydro-2-oxo-1,8-naphthyridin-3-yl]-2-(4-pyridyl)prop-2-enenitrile in the form of a bright yellow solid melting at 256–257° C. Yield 40%.

EXAMPLE 82

3-[1,2-Dihydro-1-(4-methoxyphenyl)-2-oxo-1,8-naphthyridin-3-yl]-2-(3-pyridyl)prop-2-enenitrile Formula (I): X=H; Y=O; $R_2$=4-$OCH_3$-phenyl; R=4-pyridyl; $R_1$=CN The procedure of Example 79 using 2.8 g of [1,2-dihydro-1-(4-methoxyphenyl)-2-oxo-1,8-naphthyridin-3-yl]carboxaldehyde and 1.3 ml of 3-pyridylaceto-nitrile (1.2 eq) gives 2.5 g of a yellow solid, which is purified by chromatography on a silica column (eluent: dichloromethane/ethyl ether 9/1).

This gives 1.5 g of 3-[1,2-dihydro-1-(4-methoxyphenyl)-2-oxo-1,8-naphthyridin-3-yl]-2-(3-pyridyl)prop-2-enenitrile in the form of a bright yellow solid melting at 244° C. Yield 40%.

EXAMPLE 83

3-[1,2-Dihydro-1-(4-methoxyphenyl)-2-oxo-1,8-naphthyridin-3-yl]-2-(2-pyridyl)prop-2-enenitrile Formula (I): X=H; Y=O; $R_2$=4-OCH$_3$-phenyl; R=3-pyridyl; $R_1$=CN 2.8 g of [1,2-dihydro-1-(4-methoxyphenyl)-2-oxo-1,8-naphthyridin-3-yl]carboxaldehyde are suspended in 90 ml of ethanol with 1.2 ml of 2-pyridylaceto-nitrile (1.1 eq). A solution of 0.023 g of sodium in 10 ml of ethanol (0.1 eq) is then added. The pale yellow suspension obtained is stirred for 24 h and gradually becomes bright yellow. The precipitate formed is filtered off and washed with ethanol and then ether to give 3.4 g of 3-[1,2-dihydro-1-(4-methoxy-phenyl)-2-oxo-1,8-naphthyridin-3-yl]-2-(2-pyridyl)prop-2-enenitrile in the form of an orange-yellow solid melting at 251° C. Yield 89.5%.

The following derivatives of formula (I) are prepared by this method:

| Example | X | $R_2$ | Y | $R_1$ | R | M.p. (°C.) | Yield (%) |
|---|---|---|---|---|---|---|---|
| 84 | H | 3-Cl-Phe | O | CN | 2-Py | 301 | 51 |
| 85 | H | 3-Cl-Phe | O | CN | 3-Py | 256–258 | 25 |
| 86 | H | 2-Cl-Phe | O | CN | 3-Py | 229–231 | 34 |
| 87 | H | 3-CH$_3$-Phe | O | CN | 2-Py | 284 | 53 |
| 88 | H | 3-CH$_3$-Phe | O | CN | 3-Py | 272 | 55 |
| 89 | H | 4-CH$_3$-Phe | O | CN | 3-Py | 229–232 | 25 |
| 90 | H | 3-SCH$_3$-Phe | O | CN | 3-Py | 242–244 | 81 |
| 91 | H | 3,5-Cl-Phe | O | CN | CONH$_2$ | 289 | 62 |
| 92 | H | 4-CN-Phe | O | CN | 3-Py | 262 | 38 |
| 93 | H | Phenyl | O | CN | 3-Py | 265 | 60 |
| 94 | H | 3,5-Cl-Phe | O | CN | 6-Cl-3-Py | 263.5 | 44 |
| 95 | H | 3-CF$_3$-Phe | O | CN | 3-Py | 189 | 13 |
| 96 | H | 3,5-Cl-Phe | O | CN | 2-Me-4-Thz | 312 | 68 |
| 97 | H | 3-Cl-Phe | O | CN | COOEt | 214 | 88 |
| 98 | H | 2-Cl-Phe | O | CN | COOEt | 194 | 88 |
| 99 | H | 3-Cl-Phe | O | CN | COOH | 245 | 80 |
| 100 | H | i-Pr | O | CN | 3-Py | 137–138 | 60 |
| 101 | Cl | 3,4-OCH$_3$-Bn | O | CN | 3-Py | 208 | 31 |
| 102 | H | 3,5-Cl-Phe | O | H | NO$_2$ | 269 | 23 |
| 103 | H | Cyclohexyl | O | CN | 3-Py | 216–218 | 58 |

EXAMPLE 104

[[1,2-Dihydro-1-(3-methylphenyl)-2-oxo-1,8-naphthyridin-3-yl]methylen-3-yl]oxindole Formula (I): X=H; Y=O; $R_2$=3-CH$_3$-phenyl;

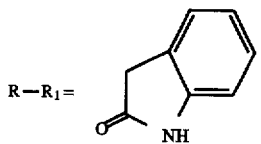

The procedure of Example 83 using 3 g of [1,2-dihydro-1-(3-methylphenyl)-2-oxo-1,8-naphthyridin-3-yl]carboxaldehyde, prepared in Example 64, gives 2.9 g of [[1,2-dihydro-1-(3-methylphenyl)-2-oxo-1,8-naphthyridin-3-yl]methylen-3-yl]oxindole in the form of an orange solid melting at >310° C. Yield 75%.

EXAMPLE 105

3-[1-(3,5-Dichlorophenyl)-1,2-dihydro-2-thioxo-1,8-naphthyridin-3-yl]-2-(3-pyridyl)prop-2-enenitrile Formula (I): X=H; Y=S; $R_2$=3,5-Cl-phenyl; R=3-pyridyl; $R_1$=CN 0.9 g of 3-[1-(3,5-dichlorophenyl)-1,2-dihydro-2-oxo-1,8-naphthyridin-3-yl]-2-(3-pyridyl)prop-2-enenitrile, prepared in Example 78, is refluxed in 15 ml of xylene with 0.23 g of phosphorus pentasulfide for 8 hours.

The medium is filtered hot and the filtrate is cooled to room temperature. The precipitate formed is filtered off and washed with ether.

This gives 0.1 g of 3-[1-(3,5-dichlorophenyl)-1,2-dihydro-2-thioxo-1,8-naphthyridin-3-yl]-2-(3-pyridyl)prop-2-enenitrile in the form of an orange solid melting at 260–261° C. Yield 10%.

EXAMPLE 106

3-[1,2-Dihydro-1-(4-hydroxyphenyl)-2-oxo-1,8-naphthyridin-3-yl]-3-hydroxy-2-(3-pyridyl)propionitrile Formula (XII): X=H; Y'=O; $R_2$=4-OH-phenyl; R=3-pyridyl; $R_1$=CN 2.7 g of [1,2-dihydro-1-(4-hydroxyphenyl)-2-oxo-1,8-naphthyridin-3-yl]carboxaldehyde, prepared in Example 75, are suspended in 90 ml of ethanol with 1.4 ml of 3-pyridylacetonitrile (1.3 eq). A solution of 0.023 g of sodium in 10 ml of ethanol (0.1 eq) is then added. The yellow suspension obtained is stirred for 24 h. The precipitate formed is filtered off and washed with ethanol and then ether to give 3.2 g of 3-[1,2-dihydro-1-(4-hydroxyphenyl)-2-oxo-1,8-naphthyridin-3-yl]-3-hydroxy-2-(3-pyridyl)propionitrile in the form of a yellow solid melting at 309° C. Yield 87%.

EXAMPLE 107

3-[1,2-Dihydro-1-(3-nitrophenyl)-2-oxo-1,8-naphthyridin-3-yl]-3-hydroxy-2-(3-pyridyl)propionitrile Formula (XII): X=H; Y'=O; $R_2$=3-NO$_2$-phenyl; R=3-pyridyl; $R_1$=CN The procedure of Example 83 using 3.0 g of [1-(3-nitrophenyl)-1,2-dihydro-2-oxo-1,8-naphthyridin-3-yl]carboxaldehyde gives 2.6 g of 3-[1,2-dihydro-1-(3-nitrophenyl)-2-oxo-1,8-naphthyridin-3-yl]-3-hydroxy-2-(3-pyridyl)propionitrile in the form of a bright yellow solid melting at 197° C. Yield 63%.

EXAMPLE 108

3-[6-Chloro-1-(3,5-dichlorophenyl)-1,2-dihydro-2-oxo-1,8-naphthyridin-3-yl]-3-hydroxy-2-(3-pyridyl)propionitrile Formula (XII): X=Cl; Y'=O; R=3-pyridyl; $R_1$=CN; $R_2$=3,5-Cl-Phe 3.8 g of [6-chloro-1-(3,5-dichlorophenyl)-1,2-dihydro-2-oxo-1,8-naphthyridin-3-yl]carboxaldehyde, prepared in Example 71, are suspended in 140 ml of methanol with 1.5 ml of 3-pyridylacetonitrile (1.3 eq). A solution of 0.023 g of sodium in 10 ml of methanol (0.1 eq) is then added. The yellow suspension obtained is stirred for 24 h. The precipitate formed is filtered off and washed with methanol and then ether to give 4.0 g of 3-[6-chloro-1-(3,5-dichlorophenyl)-1,2-dihydro-2-oxo-1,8-naphthyridin-3-yl]-3-hydroxy-2-(3-pyridyl)propionitrile in the form of a yellow solid melting at 242° C. Yield 84%.

EXAMPLE 109

3-[1,2-Dihydro-1-(4-hydroxyphenyl)-2-oxo-1,8-naphthyridin-3-yl]-2-(3-pyridyl)prop-2-enenitrile Formula (I): X=H; Y=O; $R_2$=4-OH-phenyl; R=3-pyridyl; $R_1$=CN 2.5 g of 3-[1,2-dihydro-1-(4-methoxyphenyl)-2-oxo-1,8-naphthyridin-3-yl]-2-(3-pyridyl)prop-2-enenitrile, prepared in Example 82, are dissolved in 100 ml of chloroform stabilized with amylene. The yellow solution is cooled to −40° C. and 13.2 ml of a 1 M solution of BBr₃ in dichloromethane (2 eq) are then added dropwise at this temperature, with stirring. The mixture is then left to warm up to room temperature and stirring is continued for 15 h. The reaction medium is hydrolyzed by the addition of 100 ml of water, after which the aqueous phase is separated off and extracted several times with dichloromethane. The precipitate which appears is filtered off, washed with acetone and dried to give 0.21 g of 3-[1,2-dihydro-1-(4-hydroxyphenyl)-2-oxo-1,8-naphthyridin-3-yl]-2-(3-pyridyl)prop-2-enenitrile in the form of a yellow solid melting at >317° C. Yield 9%.

EXAMPLE 110

3-[6-Chloro-1-(3,5-dichlorophenyl)-1,2-dihydro-2-oxo-1,8-naphthyridin-3-yl]-2-(3-pyridyl)prop-2-enenitrile Formula (I): X=Cl; Y=O; R₂=3,5-Cl-phenyl; R=3-pyridyl; R₁=CN The procedure of Example 78 using 2.1 g of 3-[6-chloro-1-(3,5-dichlorophenyl)-1,2-dihydro-2-oxo-1,8-naphthyridin-3-yl]-3-hydroxy-2-(3-pyridyl)propionitrile, prepared in Example 108, gives 1.9 g of 3-[6-chloro-1-(3,5-dichlorophenyl)-1,2-dihydro-2-oxo-1,8-naphthyridin-3-yl]-2-(3-pyridyl)prop-2-enenitrile in the form of a bright yellow solid melting at 279° C. Yield 94%.

EXAMPLE 111

3-[1,2-Dihydro-1-(3-nitrophenyl)-2-oxo-1,8-naphthyridin-3-yl]-2-(3-pyridyl)prop-2-enenitrile Formula (I): X=H; Y=O; R₂=3-NO₂-phenyl; R=3-pyridyl; R₁=CN The procedure of Example 78 using 4.2 g of 3-[1,2-dihydro-1-(3-nitrophenyl)-2-oxo-1,8-naphthyridin-3-yl]-3-hydroxy-2-(3-pyridyl)propionitrile, prepared in Example 107, gives 0.7 g of 3-[1,2-dihydro-1-(3-nitrophenyl)-2-oxo-1,8-naphthyridin-3-yl]-2-(3-pyridyl)prop-2-enenitrile in the form of a bright yellow solid melting at 272–274° C., after purification on a silica column (eluent: dichloromethane). Yield 18%.

EXAMPLE 112

3-[1-(3-Aminophenyl)-1,2-dihydro-2-oxo-1,8-naphthyridin-3-yl]-2-(3-pyridyl)prop-2-enenitrile Formula (I): X=H; Y=O; R₂=3-NH₂-phenyl; R=3-pyridyl; R₁=CN 0.5 g of 3-[1,2-dihydro-1-(3-nitrophenyl)-2-oxo-1,8-naphthyridin-3-yl]-2-(3-pyridyl)prop-2-enenitrile, prepared in Example 111, is suspended in 15 ml of methanol and 10 ml of water, in the presence of 0.5 g of iron powder. The suspension is heated to about 50° C. and 0.5 ml of concentrated hydrochloric acid is added dropwise. The reaction mixture is refluxed for 45 minutes and then cooled to room temperature. The residual iron is removed and the filtrate is diluted with water, treated with 0.5 g of potassium carbonate and extracted with dichloromethane. The organic phase is decanted, washed with water, dried and concentrated to give 0.2 g of 3-[1-(3-aminophenyl)-1,2-dihydro-2-oxo-1,8-naphthyridin-3-yl]-2-(3-pyridyl)prop-2-enenitrile in the form of a bright yellow solid melting at 280° C., after purification on a silica column (eluent: dichloromethane/methanol 98.5/1.5). Yield 40%.

EXAMPLE 113

N-2-(4-Chlorophenyl)ethylcyanoacetamide

Formula (X): R₁=CN;

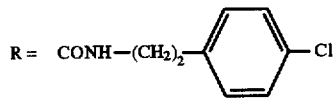

5.6 g of ethyl cyanoacetate and 7.8 g of 4-chlorophenethylamine are refluxed for 9 h in 50 ml of ethanol to give a solution. After concentration and cooling, this solution gives a residue which crystallizes. This is taken up with ether, filtered off and washed with ether to give 7.8 g of N-2-(4-chlorophenyl)ethylcyanoacetamide in the form of a white solid melting at 122° C. Yield 70%.

EXAMPLE 114

N-(3-Methylphenyl)methylcyanoacetamide

Formula (X): R₁=CN;

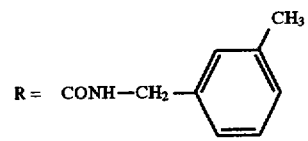

5.6 g of ethyl cyanoacetate and 6.06 g of 3-methylbenzylamine are refluxed for 9 h in 40 ml of ethanol to give a solution. After cooling, this solution gives a precipitate which is filtered off and washed with ethanol and ether to give 4.8 g of N-(3-methylphenyl)methylcyanoacetamide in the form of a white solid melting at 115° C. Yield 51%.

EXAMPLE 115

N-[2-(4-Chlorophenyl)ethyl]-2-cyano-3-[1,2-dihydro-1-(4-methoxyphenyl)-2-oxo-1,8-naphthyridin-3-yl]prop-2-enamide Formula (I): X=H; Y=O; R₂=4-OCH₃-phenyl; R₁=CN

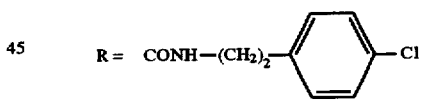

1.4 g of [1,2-dihydro-1-(4-methoxyphenyl)-2-oxo-1,8-naphthyridin-3-yl]carboxaldehyde and 1.1 g of N-[2-(4-chlorophenyl)ethyl]cyanoacetamide (1 eq), prepared in Example 113, are dissolved in 100 ml of tetrahydrofuran. 0.7 g of potassium carbonate (1 eq) is added and the reaction mixture is stirred at room temperature for 24 h. The insoluble material is filtered off, the filtrate is concentrated and the residue is taken up with hot isopropanol. After hot filtration, 0.87 g of N-[2-(4-chlorophenyl)ethyl]-2-cyano-3-[1,2-dihydro-1-(4-methoxyphenyl)-2-oxo-1,8-naphthyridin-3-yl]prop-2-enamide is obtained in the form of a yellow solid melting at 242° C. Yield 36%.

EXAMPLE 116

N-(3-Methylphenyl)methyl-2-cyano-3-[1,2-dihydro-1-(4-methoxyphenyl)-2-oxo-1,8-naphthyridin-3-yl]prop-2-enamide Formula (I): X=H; Y=O; R₂=4-OCH₃-phenyl; R₁=CN;

R = 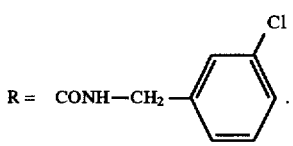

By the procedure of Example 115, 2.8 g of [1,2-dihydro-1-(4-methoxyphenyl)-2-oxo-1,8-naphthyridin-3-yl] carboxaldehyde and 1.9 g of N-(3-methylphenyl)-methylcyanoacetamide (1 eq), prepared in Example 114, react to give 0.43 g of N-(3-methylphenyl)methyl-2-cyano-3-[1,2-dihydro-1-(4-methoxyphenyl)-2-oxo-1,8-naphthyridin-3-yl]prop-2-enamide in the form of a yellow solid melting at 188° C., after purification on a silica column (eluent: cyclohexane/ethyl acetate 5/5) and recrystallization from isopropanol. Yield 9.5%.

Pharmacology

Measurement of inhibition of the balb c 3T3 fibroblast proliferation induced by a growth factor in rat aorta smooth muscle cells I. Principle Inhibition of the cell proliferation induced by a growth factor (for example PDGF) is evaluated by measuring the $^3$H-thymidine incorporation into balb c 3T3 fibroblasts.

II. Procedure

The balb c 3T3 fibroblasts are cultivated at 37° C. with 5% of $CO_2$ up to the point of subconfluence and are then placed for 24 hours under rest conditions in a serum-impoverished medium. They are subsequently pretreated for one hour with the test molecule and then stimulated for 24 hours with a growth factor (for example PDGF). $^3$H-Thymidine is incorporated over the last 2 hours. All these steps are performed at 37° C. with 5% of $CO_2$.

The reaction is terminated by sucking off the reaction medium, detaching the cells and then filtering the lyzed cells through glass fiber filters.

III. Expression of the Results

The results are expressed as the percentage inhibition of the stimulation of $^3$H-thymidine incorporation due to the action of the growth factor.

The results obtained show that the compounds of formula (I) are powerful inhibitors of the balb c 3T3 fibroblast proliferation stimulated by PDGF.

| Product of | % inhibition of the $^3$H-thymidine incorporation stimulated by PDGF in balb c 3T3 fibroblasts | | |
|---|---|---|---|
| Example | 1E - 6M | 1E - 7M | $IC_{50}$ |
| 78 | 95 | | 0.3 µM |
| 79 | 76 | | |
| 80 | 24 | | |
| 81 | 64 | 26 | 0.2 µM |
| 82 | 55 | | |
| 83 | 48 | | |
| 85 | 82 | 24 | |
| 86 | 66 | | |
| 87 | 63 | | |
| 88 | 59 | | |
| 89 | 24 | | |
| 92 | | 29 | |
| 93 | 41 | | |

TOXICOLOGY

| Product of | % inhibition of the $^3$H-thymidine incorporation stimulated by PDGF in balb c 3T3 fibroblasts | | |
|---|---|---|---|
| Example | 1E - 6M | 1E - 7M | $IC_{50}$ |
| 94 | 65 | | |
| 95 | 38 | | |
| 100 | 17 | | |
| 103 | 51 | | |
| 109 | | 18 | |
| 110 | | 54 | |
| 111 | 57 | | |

Toxicology

Preliminary studies have demonstrated the good tolerance of the compounds of formula (I) up to a dose of 300 mg/kg, administered intraperitoneally and orally to rats.

What is claimed is:

1. A naphthyridine compound of the formula:

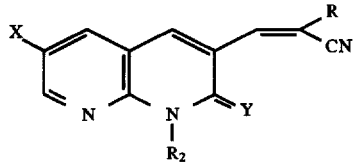

wherein X is hydrogen or halogen;
Y is oxygen, sulfur or NH; and
R is hydrogen; COOR', wherein R' is hydrogen or a lower alkyl group having 1 to 6 carbon atoms; $CONH_2$;

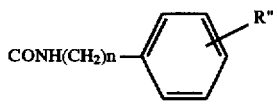

wherein n is an integer from 0 to 5; and R" is hydrogen, halogen or a lower alkyl radical having 1 to 6 carbon atoms; nitro; pyridyl, halopyridyl, thiazolyl or thiazolyl substituted by a lower alkyl radical having 1 to 6 carbon atoms; and $R_2$ is a lower alkyl group having 1 to 6 carbon atoms; a lower cycloalkyl group having 3 to 7 carbon atoms; or

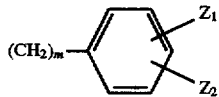

wherein m is an integer from 0 to 5; and $Z_1$ and $Z_2$ are independently hydrogen, a lower alkyl group having 1 to 6 carbon atoms, halogen, trifluoromethyl, hydroxyl, a lower alkoxy group having 1 to 6 carbon atoms, a lower thioalkyl group having 1 to 6 carbon atoms, nitro, amino or cyano; or a pharmaceutically acceptable salt thereof.

2. A compound according to claim 1, wherein X is hydrogen or chlorine.

3. A compound according to either claim 1 or claim 2, wherein Y is oxygen.

4. A compound according to either claim 1 or claim 2, wherein R is pyridyl or chloropyridyl.

5. A compound according to either claim 1 or claim 2, wherein $R_2$ is 3,5-dichlorophenyl, 4-methoxyphenyl, or 3-chlorophenyl.

6. A compound according to claim 1, which is:

3-[1-(3,5-dichlorophenyl)-1,2-dihydro-2-oxo-1,8-naphthyridin-3-yl]-2-(4-pyridyl)prop-2-enenitrile, 3-[1-(3,5-dichlorophenyl)-1,2-dihydro-2-oxo-1,8-naphthyridin-3-yl)-2-(6-chloro-3-pyridyl)prop-2-enenitrile, 3-[6-chloro-1-(3,5-dichlorophenyl)-1,2-dihydro-2-oxo-1,8-naphthyridin-3-yl]-2-(3-pyridyl)prop-2-enenitrile, 3-[1-(3-chlorophenyl)-1,2-dihydro-2-oxo-1,8-naphthyridin-3-yl]-2-(3-pyridyl)prop-2-enenitrile, or 3-[1,2-dihydro-1-(4-methoxyphenyl)-2-oxo-1,8-naphthyridin-3-yl]2-(3-pyridyl)prop-2-enenitrile.

7. A method of preparing a compound according to claim 1, which comprises heating an aldehyde of the formula:

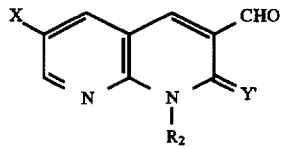

wherein X and $R_2$ are as defined in claim 1, and Y' is oxygen or NH, with an activated methylene compound of the formula:

R—CH$_2$—CN wherein R is defined in claim 1, in an alcohol in the presence of piperidine, a sodium or potassium alcoholate, or sodium or potassium carbonate.

8. A pharmaceutical composition which comprises as an active ingredient a pharmaceutically effective amount of a compound according to claim 1, or a pharmaceutically acceptable salt thereof, incorporated in a pharmaceutically acceptable excipient, vehicle or carrier.

9. A pharmaceutical composition with antiproliferative activity which contains as an active ingredient a pharmaceutically effective amount of a compound according to claim 1, or a pharmaceutically acceptable addition salt thereof, incorporated in a pharmaceutically acceptable excipient, vehicle or carrier.

10. A pharmaceutical composition according to claim 8, which is formulated as gelatin capsules or tablets containing from 1 mg to 1000 mg of the active ingredient, or as injectable preparations containing from 0.1 to 500 mg of the active ingredient.

* * * * *